United States Patent [19]

Kaiser

[11] Patent Number: 4,520,653
[45] Date of Patent: Jun. 4, 1985

[54] CIRCUITS FOR OBTAINING A VOLTAGE READING FROM A SENSING ELEMENT

[75] Inventor: William J. Kaiser, Farmington Hills, Mich.

[73] Assignee: Ford Motor Company, Dearborn, Mich.

[21] Appl. No.: 527,633

[22] Filed: Aug. 29, 1983

[51] Int. Cl.³ ............................................. G01N 27/12
[52] U.S. Cl. ........................................................ 73/23
[58] Field of Search ................ 73/23, 27 R; 324/71.5; 422/98

[56] References Cited

U.S. PATENT DOCUMENTS 3,868,846  3/1975  Kushida et al. ..................... 324/71.5
4,007,435  2/1977  Tien ........................................ 73/23
4,471,648  9/1984  Uchida et al. ........................... 73/23

Primary Examiner—Stephen A. Kreitman
Attorney, Agent, or Firm—William E. Johnson; Olin B. Johnson

[57] ABSTRACT

A circuit (10) for obtaining a voltage reading ($V_o$) from a sensing element is characterized by the following structure. A first circuit (12) connects a first end (14) of a voltage source (16) to a first end (18) of a resistance heater (20). A second circuit (22) connects a second end (24) of the voltage source to a second end (26) of the resistance heater. A sensing element (28) has two leads (30,32). A third circuit (34) connects lead (30) of the sensing element to an external circuit (36). A load resistor (40) is coupled between the second circuit and the third circuit. An interconnecting circuit (42) couples lead (32) of the sensing element intermediate the resistance heater. The electrical resistance of resistance heater is substantially less than the electrical resistance of the sensing element.

14 Claims, 4 Drawing Figures

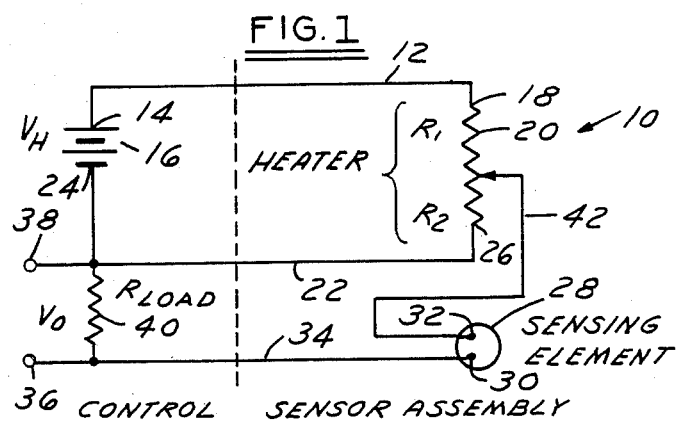
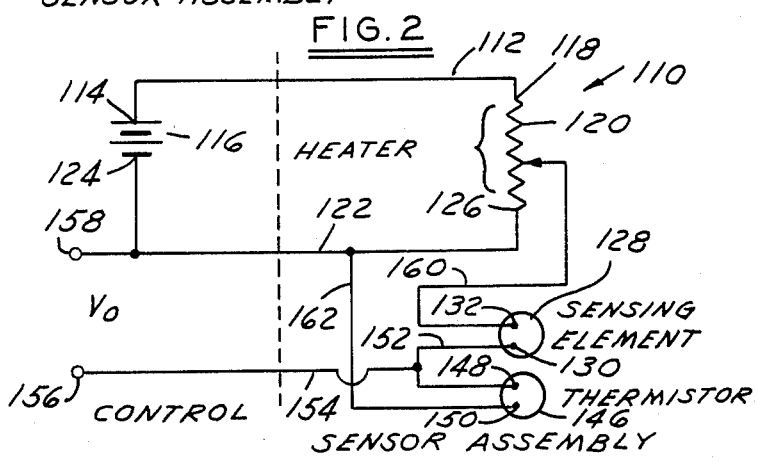
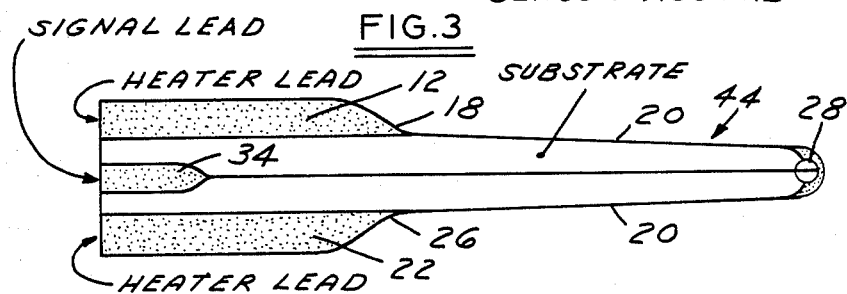
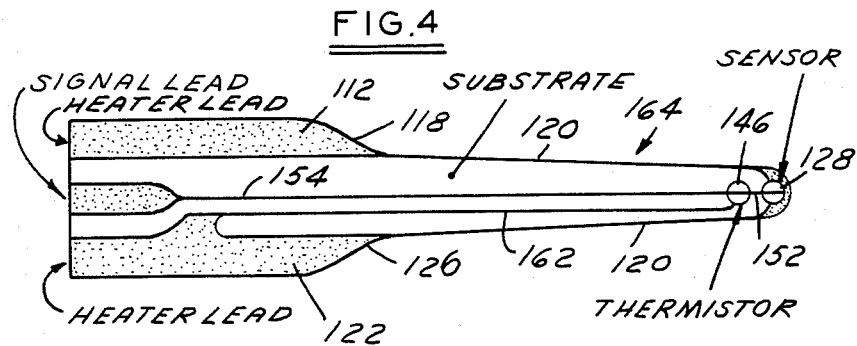

CIRCUITS FOR OBTAINING A VOLTAGE READING FROM A SENSING ELEMENT

TECHNICAL FIELD

This application is directed to circuits for obtaining a voltage reading from a sensing element. The circuits have particular utility when the sensing element is an oxygen gas sensing element used to measure the concentration of oxygen in exhaust gases from an internal combustion engine. The signal derived from such a measurement is used in controlling the feed gas composition to the internal combustion engine in a way well known in the art.

BACKGROUND ART AND PRIOR ART STATEMENT

No search was conducted on the subject matter of this specification in the U.S. Patent and Trademark Office or in any other search facility. I am unaware of any prior art more relevant to the subject matter of this specification than that which will be set forth below.

Many modern day automotive engine control systems employ oxygen gas sensors to detect the level of oxygen in the exhaust gases leaving the internal combustion engine after a combustion process therein. The oxygen sensors measure the oxygen concentration in a manner which indicates whether the exhaust gases have oxygen contained therein as oxygen or whether the gases are oxygen deficient. This indicates whether the combustion mixture being fed to the engine is rich in fuel, the exhaust gases will be oxygen deficient, or lean in fuel, the exhaust gases will have oxygen therein. By knowing whether the engine is operating rich or lean, the device metering fuel into the air going to the engine can be adjusted by electronic controls so that a proper amount of fuel is being fed to the internal combustion process.

In order to improve the accuracy of the exhaust gas sensors, it has been proposed that a heater element be used in conjunction with the sensing element so that the sensing element is always at a particular reference temperature and thus give consistent readings over long periods of time. The so-called "self-heated" oxygen sensor configuration has advantages over the unheated version by having a very short light-off time (that is, it begins to operate properly within a relatively short period of time) and greater immunity to performance instability caused by exhaust gas deposits and temperature fluctuations.

The present specification is directed to circuits which use only three wires to effect a self-heated sensor construction. The circuits disclosed herein can incorporate not only a heater, a sensing element, but also a stabilizing thermistor, and still require only three external leads.

DISCLOSURE OF THE INVENTION

This invention is directed to circuits for obtaining a voltage reading from a sensing element. The circuits of this invention function with sensing elements which are heated by a heater to an operational temperature. The circuits of this invention are detailed below.

A particular circuit for obtaining a voltage reading from a sensing element is characterized in the following manner. A first end of a voltage source is connected by a first circuit to a first end of a resistance heater. A second circuit connects a second end of the voltage source to a second end of the resistance heater. A sensing element having two leads is provided. A third circuit connects a first one of the leads of the sensing element to an external circuit. A load resistor is coupled between the second circuit and the third circuit. An interconnecting circuit is also provided which couples a second one of the leads of the sensing element intermediate the resistance heater. The electrical resistance of the resistance heater is substantially less than the electrical resistance of the sensing element. The first circuit, second circuit, and third circuit are the three leads from the heated sensing element. The sensing element may be an oxygen gas sensing element and, in particular, may be a titania oxygen gas sensing element.

In another variation of the circuit, the interconnecting circuit connects a second one of the leads of the sensing element to the first circuit before the resistance heater rather than intermediate the resistance heater.

The circuit of this invention may also be used with a sensing element which has a thermistor in series therewith. The self-heated oxygen sensor may lack the ability to maintain a constant and reproducible sensing element temperature. It is necessary therefore to incorporate a thermistor (temperature compensation) element into the self-heated sensor configuration.

When such a thermistor is provided, the circuit for obtaining a voltage reading from a sensing element is characterized in the following manner. A first circuit connects a first end of a voltage source to a first end of a resistance heater. A second circuit connects a second end of the voltage source to a second end of the resistance heater. A sensing element and a thermistor are provided, both of said latter mentioned elements each having two leads. A first interconnecting circuit couples a first lead of the sensing element to a first lead of the thermistor. A third circuit connects the first interconnecting circuit to an external circuit. A second interconnecting circuit couples a second one of the leads of the sensing element intermediate the resistance heater. A third interconnecting circuit couples a second lead of the thermistor to the second circuit. The electrical resistance of the resistance heater is substantially less than the electrical resistance of the sensing element.

Once again, in the case of this circuit, the sensing element can be an oxygen gas sensing element and, in particular, can be a titania oxygen gas sensing element. Also, it is possible that the second interconnecting circuit couples the second of the leads of the sensing element to the first circuit before the resistance heater. This coupling would be instead of the coupling intermediate the resistance heater.

Also in this circuit, the positions of the sensing element and the thermistor may be interchanged. In such a case, the second interconnecting circuit would couple a second one of the electrical leads of the thermistor intermediate the resistance heater or alternatively to the first circuit. The third interconnecting circuit would couple a second lead of the sensing element to the second circuit.

BRIEF DESCRIPTION OF THE DRAWINGS

The novel features that are considered characteristic of this invention are set forth with particularity in the appended claims. The invention itself, however, both as to its organization and its method of operation, together with additional objects and advantages thereof, will best be understood from the following description of specific embodiments when read in connection with the FIG. 1 is an electrical schematic of a circuit according to this invention including a heater and a sensing element;

FIG. 2 is an electrical schematic of a circuit according to this invention including a heater, a sensing element, and a thermistor;

FIG. 3 is a sensor assembly having the circuit of FIG. 1 placed thereon; and

FIG. 4 is a sensor assembly having the circuit of FIG. 2 placed thereon.

BEST MODE AND INDUSTRIAL APPLICABILITY

The following description is what I consider to be a preferred embodiment of the circuit for obtaining a voltage reading from a sensing element in accordance with my invention. The following description also sets forth what I now contemplate to be the best mode of constructing my inventive circuit. The description is not intended to be a limitation upon the broader principles of this construction, and while preferred materials are used to form the construction in accordance with a requirement of the laws, it does not mean that other materials cannot be used to make the devices embodying my inventive circuit.

The conventional resistive type air/fuel ratio sensor assembly sometimes includes a resistive heating element adjacent to the sensing element to stabilize the sensing element at an elevated temperature. Those skilled in the art know that such air/fuel ratio sensors are used as a means for controlling the air/fuel mixture being fed to an internal combustion engine such as the type of engine which powers many motor vehicles. Normally, the conventional resistive type sensor has a voltage applied to both the heating element and another voltage to a resistor which is in series with the sensing element. In this case, four interconnecting leads are required to link the sensor assembly to the control module. Normally, the length of leads are substantial since the sensor assembly and the control module are normally at opposite ends of the motor vehicle.

The circuits of my invention reduce the number of leads which are required for a heated sensing element by one. In my circuits, the heated sensor assembly is one in which the sensing element and the heating element are electrically connected and only three interconnecting leads are required between the sensor and any control module.

Reference is made to FIG. 1, which shows a preferred circuit of my invention for use in a situation where the circuit includes both a heater and a sensing element. In FIG. 1 there is shown a circuit, generally identified by the numeral 10, for obtaining a voltage reading $V_o$ from a sensing element. The circuit is characterized in the following manner. A first circuit 12 interconnects a first end 14 of a voltage source 16 to a first end 18 of a resistance heater 20. A second circuit 22 interconnects a second end 24 of the voltage source 16 to a second end 26 the resistance heater 20. Normally, the voltage source is a standard 12 volt battery. However, the voltage source can also be a voltage source which has additional circuitry associated therewith so that a constant current is supplied by the voltage source.

A sensing element 28 is provided which has a pair of leads 30 and 32 associated therewith. In the situation where the circuit is being used to detect changes in the air/fuel ratio of a feed gas stream to an automotive engine by checking the amount of oxygen contained in the exhaust products produced by burning the feed gas stream, the sensing element 28 is generally an oxygen gas sensing element. In particular, we prefer to use a titania sensor for sensing changes in the air/fuel ratio from conditions in which an excessive amount of oxygen is present to conditions in which an oxygen deficient condition exists and vice-versa. A third circuit 34 connects the lead 30 of the sensing element 28 to an external circuit 36. The first circuit 12, second circuit 22, and third circuit 34 are the circuit leads which extend from the sensor assembly to the control module for the assembly. These, in effect, are the three leads from the sensor assembly, positioned in the exhaust tailpipe, to the control module which is located near the device feeding the fuel mixture to the engine to be burned.

The second circuit 22 also leads to an external circuit 38. A load resistor 40 is coupled across the second circuit 22 and the third circuit 34. A voltage reading $V_o$ may be taken between the external circuits 36 and 38 to monitor the resistance of the sensing element 28 which varies in response to the conditions it is subjected to. The voltage reading $V_o$ is large when the sensor element resistance is less than the load resistance. The voltage reading $V_o$ is nearly zero when the sensor element resistance is much greater than the load resistance. In the case of a $TiO_2$ sensor, the sensing element resistance is small under rich engine operating conditions and is large under lean conditions.

An interconnecting circuit 42 couples lead 32 of the sensing element 28 to a position intermediate the resistance heater 20. The electrical resistance of the resistance heater is substantially less than the resistance of the sensing element, even at its lowest resistance value. Normally, the sensing element is one which has a substantial change in resistance due to a change in a particular condition. For the sensor circuits described here, the resistance of the heater element would be generally much less than that of the sensing element, thermistor element, or load resistor. This will generally be the case because the heater current must be primarily limited to a path through the heater.

As an optional circuit, the interconnecting circuit 42 may connect the lead 32 of the sensing element 28 to the first circuit 12 rather than at a position intermediate the resistance heater 20. Also, when I say that the connection is made intermediate, I mean that the connection can be anyplace along the length of the resistance heater between the first end 18 and the second end 26 thereof.

FIG. 3 illustrates the production of the sensor assembly in a preferred embodiment. In this situation, a suitable ceramic substrate 44 is processed through a silk screen printing operation to form on the substrate a first circuit 12 which is connected at a first end 18 to the resistance heater 20 as well as a second circuit 22 which is connected to the second end 26 of the resistance heater 20. The resistance heater 20 is, in essence, a very thin line of printed material (for example, platinum) which, because of its thinness, increases the resistance to electrical flow therethrough.

At the tip of the substrate 44, a titania dioxide sensing element 28 is placed directly on top of the resistance heater 20 which, in essence, accomplishes the interconnection of the sensor assembly intermediate the heater. The third circuit 34 is then placed on the substrate 44 in a silk screening operation in a manner that it has an enlarged portion near the left hand end of the substrate and then a necked down narrow portion which extends along the length of the substrate and overlies the top of the sensing element 28. Thus the sensor assembly has the heater and sensing element connected by three leads or circuits 12, 22, and 34 to the control module.

In FIG. 2, there is a circuit schematic of a circuit for obtaining a voltage reading from a sensing element for a circuit which also includes a thermistor for protecting the sensing element. This circuit is generally identified by the numeral 110 and it includes a first circuit 112 for connecting a first end 114 of a voltage source 116 to a first end 118 of a resistance heater 120. A second circuit 122 connects a second end 124 of the voltage source 116 to a second end 126 of the resistance heater 120. A sensing element 128 is provided which has leads 130 and 132 associated therewith. A thermistor 146 is also provided which has two leads 148 and 150 associated therewith. A first interconnecting circuit 152 couples the first lead 130 of the sensing element 128 to the first lead 148 of the thermistor 146. A third circuit 154 connects the first interconnecting circuit 152 to an external circuit 156. The second circuit 122 is also connected to an external circuit 158 across which the voltage $V_o$ can be measured.

A second interconnecting circuit 160 connects the lead 132 of the sensing element 128 to a location intermediate the resistance heater 120. As in the case with the first circuit, an optional provision is that the interconnecting circuit 160 can connect the lead 132 of the sensing element 128 to the first circuit 112 (this embodiment not being shown in the drawings).

A third interconnecting circuit 162 interconnects the lead 150 of the thermistor 146 to the second circuit 122 to complete the circuitry. Once again, the sensor assembly is provided with three external leads. In this case, the three external leads or circuits are the first circuit 112, the second circuit 122, and the third circuit 154.

In the preferred embodiment, when this circuit is used in association with an exhaust gas sensor, the sensing element 128 would be a titania sensor and the thermistor 146 would be an oxygen insensitive material with a temperature coefficient of resistance equal to that of titania. Once again, in this situation, the resistance of these element is substantially greater than the resistance of the heater, as was described for the circuit embodiment shown in FIG. 1.

The sensor assembly portion of FIG. 2 is shown in FIG. 4 as being placed on a suitable substrate 164. In this case, the first circuit 112 and second circuit 122 are laid down at the same time along with the resistance heater 120. After the resistance heater has been laid down, the sensor 128 is deposited on top of the resistance heater at approximately its mid-point. The third circuit 154 and first interconnecting circuit 152 are then laid down on the substrate 164. After application of these circuits, the thermistor 146 is placed on top of this combined circuit 154 and 152 so that it is in electrical contact therewith. The third interconnecting circuit 162 is then laid down so that it contacts on one end the thermistor 146 and at the other end the second circuit 122. This completes the sensor assembly portion of the circuit shown in FIG. 2 and provides for the three external leads or circuits, namely, first circuit 112, second circuit 122, and third circuit 154.

As an alternate to the design shown in FIGS. 2 and 4, the position of the sensing element 128 and thermistor 146 may be interchanged without interchanging the function of these elements or in any other way altering the same.

While particular embodiments of the circuits of this invention have been illustrated and described, it will be obvious to those skilled in the art that various changes and modifications may be made without departing from the invention, and it is intended to cover in the appended claims all such modifications and equivalents as fall within the true spirit and scope of this invention.

I claim:

1. A circuit for obtaining a voltage reading from a sensing element, characterized by:

a voltage source;

a resistance heater;

first circuit means for connecting a first end of said voltage source to a first end of said resistance heater;

second circuit means for connecting a second end of said voltage source to a second end of said resistance heater;

a sensing element having two leads;

third circuit means for connecting a first one of said leads of said sensing element to an external circuit;

a load resistor coupled between said second circuit means and said third circuit means; and interconnecting circuit means for coupling a second one of said leads of said sensing element intermediate said resistance heater;

said electrical resistance of said resistance heater being substantially less than said electrical resistance of said sensing element.

2. The circuit of claim 1, wherein said sensing element is an oxygen gas sensing element.

3. The circuit of claim 1, wherein said sensing element is a titania oxygen gas sensing element.

4. A circuit for obtaining a voltage reading from a sensing element, characterized by:

a voltage source;

a resistance heater;

first circuit means for connecting a first end of said voltage source to a first end of said resistance heater;

second circuit means for connecting a second end of said voltage source to a second end of said resistance heater;

a sensing element having two leads;

third circuit means for connecting a first one of said leads of said sensing element to an external circuit;

a load resistor coupled between said second circuit means and said third circuit means; and interconnecting circuit means for coupling a second one of said leads of said sensing element to said first circuit means;

said electrical resistance of said resistance heater being substantially less than said electrical resistance of said sensing element.

5. The circuit of claim 4, wherein said sensing element is an oxygen gas sensing element.

6. The circuit of claim 4, wherein said sensing element is a titania oxygen gas sensing element.

7. A circuit for obtaining a voltage reading from a sensing element, characterized by:

a voltage source;

a resistance heater;

first circuit means for connecting a first end of said voltage source to a first end of said resistance heater;

second circuit means for connecting a second end of said voltage source to a second end of said resistance heater;
a sensing element having two leads;
a thermistor having two leads;
first interconnecting circuit means for coupling a first lead of said sensing element to a first lead of said thermistor;
third circuit means for connecting said first interconnecting circuit means to an external circuit;
second interconnecting circuit means for coupling a second one of said leads of said sensing element intermediate said resistance heater; and
third interconnecting circuit means for coupling a second lead of said thermistor to said second circuit means;
said electrical resistance of said resistance heater being substantially less than said electrical resistance of said sensing element.

8. The circuit of claim 7, wherein said sensing element is an oxygen gas sensing element.

9. The circuit of claim 7, wherein said sensing element is a titania oxygen gas sensing element.

10. The circuit of claim 7, wherein said second interconnecting circuit means is for coupling said second one of said leads of said sensing element to said first circuit means before said resistance heater.

11. A circuit for obtaining a voltage reading from a sensing element, characterized by:
a voltage source;
a resistance heater;
first circuit means for connecting a first end of said voltage source to a first end of said resistance heater;
second circuit means for connecting a second end of said voltage source to a second end of said resistance heater;
a sensing element having two leads;
a thermistor having two leads;
first interconnecting circuit means for coupling a first lead of said sensing element to a first lead of said thermistor;
third circuit means for connecting said first interconnecting circuit means to an external circuit;
second interconnecting circuit means for coupling a second one of said electrical leads of said thermistor intermediate said resistance heater; and
third interconnecting circuit means for coupling a second lead of said sensing element to said second circuit means;
said electrical resistance of said resistance heater being substantially less than said electrical resistance of said sensing element.

12. The circuit of claim 11, wherein said sensing element is an oxygen gas sensing element.

13. The circuit of claim 11, wherein said sensing element is a titania oxygen gas sensing element.

14. The circuit of claim 11, wherein said second interconnecting circuit means is for coupling said second one of said leads of said sensing element to said first circuit means before said resistance heater.

* * * * *